United States Patent [19]

Bussmann

[11] Patent Number: 5,475,164
[45] Date of Patent: Dec. 12, 1995

[54] PROCESS FOR PREPARING 3-FLUORO-4,6-DICHLOROTOLUENE

[75] Inventor: Werner Bussmann, Leverkusen, Germany

[73] Assignee: Bayer Aktiengesellschaft, Leverkusen, Germany

[21] Appl. No.: 343,796

[22] Filed: Nov. 22, 1994

[30] Foreign Application Priority Data

Dec. 1, 1993 [DE] Germany ............ 43 40 854.0

[51] Int. Cl.$^6$ .......... C07C 17/04; C07C 17/383; C07C 17/395; C07C 25/13
[52] U.S. Cl. ............ 570/144; 570/143
[58] Field of Search .............. 570/143, 144

[56] References Cited

U.S. PATENT DOCUMENTS

| | | |
|---|---|---|
| 1,946,040 | 2/1934 | Stoesser et al. . |
| 3,234,292 | 2/1966 | Robota et al. ............ 570/144 |
| 4,439,620 | 3/1984 | Klauke et al. . |
| 4,769,503 | 9/1988 | Parg et al. ............ 570/144 |
| 4,851,596 | 7/1989 | Mais et al. . |

FOREIGN PATENT DOCUMENTS

| | | |
|---|---|---|
| 45430 | 2/1982 | European Pat. Off. ............ 570/143 |
| 3142856 | 5/1983 | Germany . |
| 0292824 | 11/1988 | Germany . |
| 0114604 | 8/1994 | Germany . |

OTHER PUBLICATIONS

English translation of 0 114 604 (1994).

*Primary Examiner*—Joseph E. Evans
*Attorney, Agent, or Firm*—Sprung Horn Kramer & Woods

[57] ABSTRACT

3-Fluoro-4,6-dichlorotoluene is prepared with reduced formation of 3-fluoro-2,6-dichlorotoluene by chlorinating 3-fluorotoluene in the presence of a catalyst system to give a mixture containing 3-fluoro-6-chlorotoluene and 3-fluoro-4-chlorotoluene and chlorinating this in the presence of another catalyst system to give 3-fluoro-4,6-dichlorotoluene.

11 Claims, No Drawings

PROCESS FOR PREPARING 3-FLUORO-4,6-DICHLOROTOLUENE

The present invention relates to a process for preparing 3-fluoro-4,6-dichlorotoluene by two-stage selective chlorination of 3-fluorotoluene, with a reduced proportion of the by-product 3-fluoro-2,6-dichlorotoluene being obtained.

3-Fluoro-4,6-dichlorotoluene is a precursor for the preparation of 2,4-dichlorobenzoyl chloride, a key product for the preparation of antiseptics of the quinolonecarboxylic acid type. A series of synthetic routes have been described for the preparation of this compound, however these either give unsatisfactory yields or they involve using intermediates and products which can be handled only with difficulty in industry.

It is known that 3-fluoro-4,6-dichlorotoluene can be prepared from 3-amino-4,6-dichlorotoluene (see DE-A1-3 142 856). Although this gives good yields, the preparation by this route involves the handling of a triazene compound which decomposes easily.

Our own experiments on the single-stage dichlorination of 3-fluorotoluene in the presence of Friedel-Crafts catalysts and sulphur or thiazepine compounds have indicated that this gives mixtures of 3-fluoro-4,6-dichlorotoluene and 3-fluoro-2,6-dichlorotoluene which contain at most only 66 mol % of the 4,6 isomer.

A process has now been found for preparing 3-fluoro-4,6-dichlorotoluene with reduced formation of 3-fluoro-2,6-dichlorotoluene, which is characterized in that 3-fluorotoluene is chlorinated in the presence of Friedel-Crafts catalysts and sulphur to give a mixture containing 3-fluoro-6-chlorotoluene and 3-fluoro-4-chlorotoluene and this is chlorinated in the presence of Friedel-Crafts catalysts and thiazepine compounds to give 3-fluoro-4,6-dichlorotoluene.

Surprisingly, the selectivity of the formation of 3-fluoro-4,6-dichlorotoluene is higher if, instead of in a single-stage process, according to the invention the monochloro derivative is first prepared using a catalyst system, and then further chlorination to give the dichloro derivative is carried out using another catalyst system.

Suitable Friedel-Crafts catalysts for both reaction stages of the process of the invention are, for example, the usual metal and transition metal halides. Preference is given to iron(III) chloride, antimony(III) and (V) chloride and aluminium chloride, particular preference is given to iron(III) chloride. Identical or different Friedel-Crafts catalysts can be used in the two reaction stages. Preference is given to using the same Friedel-Crafts catalysts in both reaction stages.

In the first reaction stage, from 0.05 to 5% by weight (based on 3-fluorotoluene) of Friedel-Crafts catalysts can, for example, be used. This amount is preferably from 0.1 to 1% by weight.

Sulphur can, for example, be used in an amount of from 0.05 to 5% by weight (based on 3-fluorotoluene). This amount is preferably from 0.1 to 1% by weight. The sulphur can be used in commercial pulverulent form.

Both reaction stages of the process of the invention can be carried out in the presence or absence of solvents. Suitable solvents are, for example, halogenated aliphatic hydrocarbons such as carbon tetrachloride or dichloromethane and also, in particular for the second reaction stage, longer-chain halogenated aliphatic hydrocarbons having correspondingly higher boiling points. Both reaction stages are preferably carried out without addition of solvents.

The first reaction stage can, for example, be carried out at from 0° to 60° C. and, for example, from 0.8 to 1.1 mol of chlorine can be introduced per mol of 3-fluorotoluene. The reaction stage is preferably carried out at from 10° to 30° C. and using from 0.95 to 1.01 mol of chlorine; it is particularly preferably carried out at room temperature and using one mol of chlorine.

After completion of the first reaction stage of the process of the invention, the catalyst system is separated off. This can be achieved, for example, by decantation or filtration or by distilling off the reaction products. The catalyst system can be reused in a further batch.

If desired, before or after separating off the catalyst system, any hydrogen chloride still present can be blown out using an inert gas, for example using nitrogen. It is advantageous, prior to the second reaction stage, to separate off any low-boiling by-products, in particular volatile sulphur compounds, which may interfere in the second stage. If the reaction products are separated off from the catalyst system by distillation a first fraction containing these by-products can be separated off in this distillation. Otherwise, for example, a small part, for example from 10 to 20% by weight, can be distilled out of the reaction mixture freed of the catalyst system.

The separated-off, low-boiling by-products or a fraction containing them can be reused in a further batch.

The reaction mixture obtained after the first reaction stage generally contains 3-fluoro-6-chlorotoluene and 3-fluoro-4-chlorotoluene in a weight ratio of 85–92:7–3. Based on 3-fluorotoluene used, the yields of this mixture are generally above 95%. They are frequently almost quantitative.

The reaction mixture of the first reaction stage, freed of the catalyst system and preferably worked up as described above, is then fed to the second reaction stage.

In the second reaction stage, from 0.1 to 10% by weight (based on 3-fluoro-chlorotoluene) of Friedel-Crafts catalysts can, for example, be used. This amount is preferably from 0.2 to 2.5% by weight.

Suitable thiazepine compounds are, for example, those described in EP-A1-292 824 (=U.S. Pat. No. 4,851,596). They preferably correspond to one of the formulae (I) to (VII) below

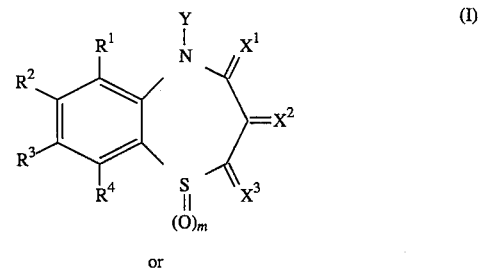

(I)

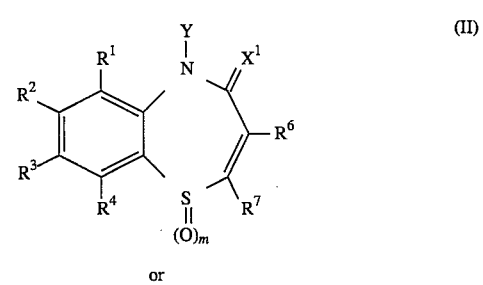

(II)

or

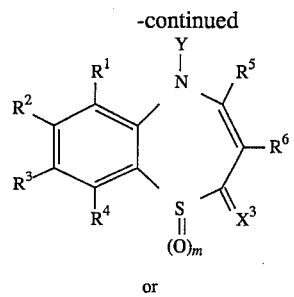

or

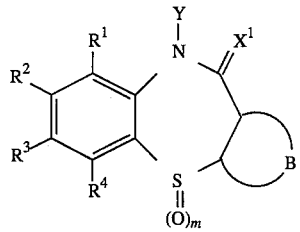

or

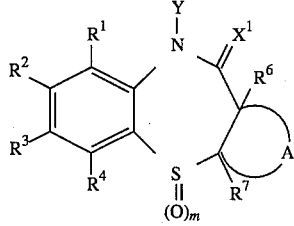

or

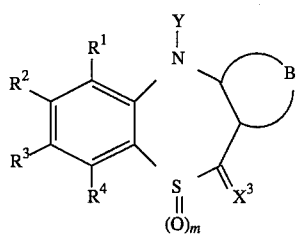

or

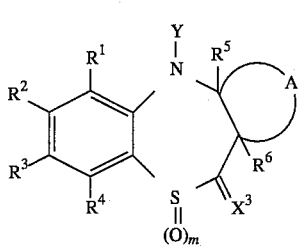

in which $R^1$, $R^2$, $R^3$, $R^4$ are identical or different and represent hydrogen, hydroxy, amino, cyano, halogen, nitro, nitroso, sulphonyl, sulphoxyl, tosyl, mercapto, carboxyl, carboxyamide, carbalkoxy, dithiocarboxyl, thiocarboxylamide, dithiocarbalkoxy, optionally substituted alkyl, aryl, heteroaryl, alkoxy, aryloxy, heteroaryloxy, acyloxy, alkylthio, arylthio, heteroarylthio, acylthio, acyl, thioacyl or acylamino or among one another form one or more saturated or unsaturated, optionally substituted isocyclic or heterocyclic carbon rings having up to 8 carbon atoms, Y is hydrogen, optionally substituted alkyl, aryl, heteroaryl, acyl, thioacyl, acyloxy, arylamino or acylamino, $X^1$, $X^2$ and $X^3$ are, independently of one another, each one of the following groups:

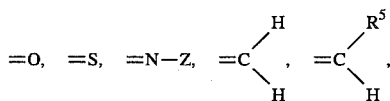

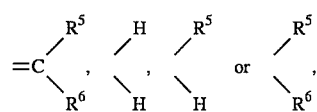

$R^5$, $R^6$ and $R^7$ are identical or different and are as defined for $R^1$ to $R^4$, with the exception that they do not form a cyclic ring among one another, Z is as defined for Y, with the exception that Z is not H, A represents the anellation of an optionally substituted, saturated, isocyclic or heterocyclic ring having up to 8 carbon atoms, represents the anellation of an optionally substituted, unsaturated, isocyclic or heterocyclic ring having up to 8 carbon atoms, and m is 0 or 1.

Possible substituents of the abovementioned radicals are, for example: halogen, nitro, alkoxy, alkyl, aryl and hetaryl, preference being given to halogen and alkyl.

Preferred alkyl radicals are those having from 1 to 16 carbon atoms, in particular from 1 to 4 carbon atoms.

Preferred aryl radicals are those having from 6 to 10 carbon atoms, in particular 6 and 7 carbon atoms.

Preferred heteroaryl radicals are those having from 4 to 10 atoms, from 1 to 3 of these being nitrogen, oxygen and/or sulphur atoms.

Preferred alkoxy radicals are those having from 1 to 6 carbon atoms, in particular from 1 to 4 carbon atoms.

Preferred aryloxy radicals are those having from 6 to 10 carbon atoms, in particular 6 and 7 carbon atoms.

Preferred heteroaryloxy radicals are those having from 4 to 10 atoms, 1 or 2 of these being nitrogen, oxygen and/or sulphur atoms.

Preferred acyloxy radicals are those having from 1 to 7 carbon atoms, in particular from 1 to 4 carbon atoms.

Preferred alkylthio radicals are those having from 1 to 6 carbon atoms, in particular from 1 to 4 carbon atoms.

Preferred arylthio radicals are those having from 4 to 7 carbon atoms.

Preferred heteroarylthio radicals are those having from 4 to 10 carbon atoms, 1 or 2 of which being nitrogen, oxygen and/or sulphur atoms.

Preferred acylthio, acyl and thioacyl radicals are in each case those having from 1 to 7 carbon atoms.

Preferred acylamino radicals are those having from 1 to 8 carbon atoms.

The rings A and B can, independently of one another, each contain, for example, from 1 to 3 nitrogen, oxygen and/or sulphur atoms.

Preferred halogens are fluorine, chlorine and bromine.

Very particularly preferred thiazepine compounds are:
2,3-dihydro-5H-benzo[b][1,4]thiazepin-4-one,
2-methyl-2,3-dihydro-5H-benzo[b][1,4]thiazepin-4-one,
2-ethyl-2,3-dihydro-5H-benzo[b][1,4]thiazepin-4-one,
2-propyl-2,3-dihydro-5H-benzo[b][1,4]thiazepin-4-one,
3-methyl-2,3-dihydro-5H-benzo[b][1,4]thiazepin-4-one,
2,3-dimethyl-2,3-dihydro-5H-benzo[b][1,4]thiazepin-4-one, 5-methyl-2,3-dihydro-5H-benzo[b][1,4]thiazepin-4-one,
5-benzyl-2,3-dihydro-5H-benzo[b][1,4]thiazepin-4-one,
5-acetyl-2,3-dihydro-5H-benzo[b][1,4]thiazepin-4-one,
5-chlorocarbonyl-2,3-dihydro-5H-benzo[b][1,4]thiazepin-4-one,
2-methyl-5-acetyl-2,3-dihydro-5H-benzo[b][1,4]thiazepin-4-one,
7-chloro-2,3-dihydro-5H-benzo[b][1,4]thiazepin-4-one,
6,8-dichloro-2,3-dihydro-5H-benzo[b][1,4]thiazepin-4-one,
6,8-dichloro-2,3-dimethyl-2,3-dihydro-5H-benzo[b][1,4]thiazepin-4-one,
7-methyl-2,3-dihydro-5H-benzo[b][1,4]thiazepin-4-one,
7-trifluoromethyl-2,3-dihydro-5H-benzo[b][1,4]thiazepin-4-one,
6,8-dimethyl-2,3-dihydro-5H-benzo[b][1,4]thiazepin-4-one,
2,3-dihydro-5H-[2,3]naphthaleno[b][1,4]thiazepin-4-one,
5H-dibenzo[b,f][1,4]thiazepin-4-one,
ring-chlorinated 5H-dibenzo[b,f][1,4]thiazepin-4-one,
3-tetramethylene-2,3-dihydro-5H-benzo[b][1,4]thiazepin-4-one,
6,8-dimethyl-2,3-tetramethylene-2,3-dihydro-5H-benzo[b][1,4]thiazepin-4-one,
3H-5H-benzo[b][1,4]thiazepine-2,4-dione,
3H-5H-benzo[b][1,4]thiazepin-2-one-4-thione,
3H-5H-benzo[b][1,4]thiazepine-2,4-dithione,
2,3-dihydro-5H-benzo[b][1,4]thiazepine-4-thione,
2-methyl-2,3-dihydro-5H-benzo[b][1,4]thiazepine-4-thione,
5-acetyl-2,3-dihydro-5H-benzo[b][1,4]thiazepine-4-thione,
1-oxo-2,3-dihydro-5H-1$\lambda^4$-benzo[b][1,4]thiazepine-4-thione,
1-oxo-7-chloro-5-methyl-2,3-dihydro-5H-1$\lambda^4$-benzo[b][1,4]thiazepine-4-thione,
1-oxo-2,3-dimethyl-2,3-dihydro-5H-1$\lambda^4$-benzo[b][1,4]-thiazepin-4-one,
3-acetoxy-2,3-dihydro-5H-benzo[b][1,4]thiazepin-4-one,
3-acetamino-2,5-dihydro-5H-benzo[b][1,4]thiazepin-4-one,
2,3,4,5-tetrahydro-benzo[b][1,4]thiazepine,
2,3-dimethyl-2,3,4,5-tetrahydro-benzo[b][1,4]thiazepine,
5-ethyl-2,3,4,5-tetrahydro-benzo[b][1,4]thiazepine,
2-n-tridecyl-2,3-dihydro-5H-benzo[b][1,4]thiazepin-4-one,
5-n-pentyl-2,3-dihydro-5H-benzo[b][1,4]thiazepin-4-one,
8-methoxy-2,3-dihydro-5H-benzo[b][1,4]thiazepin-4-one,
8-ethoxy-2,3-dihydro-5H-benzo[b][1,4]thiazepin-4-one,
8-methyl-2,3-dihydro-5H-benzo[b][1,4]thiazepin-4-one,
8-chloro-6-methyl-2,3-dihydro-5H-benzo[b][1,4]thiazepin-4-one,
7,9-dimethoxy-2,3-dihydro-5H-benzo[b][1,4]thiazepin-4-one,
7,9-dimethyl-2,3-dihydro-5H-benzo[b][1,4]thiazepin-4-one,
7,8-dimethyl-2,3-dihydro-5H-benzo[b][1,4]thiazepin-4-one,
7-methoxy-2,3-dihydro-5H-benzo[b][1,4]thiazepin-4-one,
7,9-dimethyl-2,3-tetramethylene-2,3-dihydro-5H-benzo[b][1,4]thiazepin-4-one,
2,3-dihydro-5H-[1,2]naphthaleno[b][1,4]thiazepin-4-one,
2,3,7,9-tetramethyl-2,3-dihydro-5H-benzo[b][1,4]thiazepin-4-one.

It is also possible to use a plurality of thiazepine compounds together.

Thiazepine compounds can be used, for example, in an amount of from 0.02 to 2% by weight (based on 3-fluorochlorotoluenes). This amount is preferably from 0.04 to 1% by weight.

The second reaction stage can, for example, be carried out at from 50° to 120° C., introducing, for example, from 0.8 to 1.0 mol of chlorine per mol of 3-fluoro-chlorotoluenes. It is preferably carried out at from 60° to 100° C. and using from 0.95 to 0.98 mol of chlorine.

The pressure while carrying out the first and second reaction stage of the process of the invention can, for example, be in the range from 1 to 10 bar. Preference is given to atmospheric pressure.

The elemental chlorine can, in both reaction stages, be introduced in gaseous or liquid form.

After completion of the second reaction stage, the catalyst system is separated off and any hydrogen chloride present is blown out, for example in the manner described above for the first reaction stage. The generally less valuable Friedel-Crafts catalyst can also be removed by single or multiple washing with water and the remaining reaction mixture can then be worked up by distillation. During this procedure, the valuable thiazepine compounds remain in the distillation residue and can, optionally together with the residue, be used again.

The separation of the two isomers present in the reaction mixture (3-fluoro-4,6-dichlorotoluene and 3-fluoro-2,6-dichlorotoluene) is possible by known methods, for example by distillation. If 3-fluoro-4,6-dichlorobenzoyl chloride is to be prepared from 3-fluoro-4,6-dichlorotoluene, the isomer separation can also be carried out only after the side-chain chlorination from the benzal chloride/benzotrichloride mixture.

The process of the invention for preparing 3-fluoro-4,6-dichlorotoluene has a series of advantages. Thus, in conventional industrial plants and using readily available chemicals, it can provide 3-fluoro-4,6-dichlorotoluene in amounts as large as desired and thereby make available precursors for active compounds of the quinolonecarboxylic acid group which are of steadily increasing importance.

It is extremely surprising that the 2-stage process of the invention gives reaction mixtures having a significantly increased content of 3-fluoro-4,6-dichlorotoluene.

EXAMPLES

Example 1

A 4-neck flask fitted with stirrer, reflux condenser, thermometer and gas inlet tube was charged with 110 g of 3-fluorotoluene. After addition of 220 mg of iron(III) chloride and 110 mg of sulphur, chlorine was introduced in an amount of 10 l/h at 20° C. (cooling with a waterbath) while stirring. After 20 hours, the reaction mixture contained 91.4% by weight of 3-fluoro-6-chlorotoluene and 5% by weight of 3-fluoro-4-chlorotoluene. The reaction mixture was subjected to distillation, with a first fraction of 20 g being taken off and recirculated to the next batch. The main fraction (120 g) contained the catalyst-free 3-fluorochlorotoluene mixture. The remaining residue was likewise reused.

The example was repeated five times, finally giving a yield of 98% for the 3-fluoro-chlorotoluene mixture.

Example 2

The same apparatus as described in Example 1 was charged with 100 g of the 3-fluoro-chlorotoluene mixture obtained as described in Example 1, and 750 mg of iron(III) chloride and 150 mg of 2,3-dihydro-5H-benzo[b][1,4]thiazepin-4-one were added. The mixture was then heated to 80° C. by means of a heating mantle and chlorine was introduced in the manner described above until only 5% by weight of the 3-fluoro-6-chlorotoluene used was present. The reaction mixture was washed twice with water (20 ml each time) and subsequently distilled. This gave a first fraction which essentially contained unreacted starting material and which was reused in a further batch. 100 g (=90% of theory) of a mixture of 76% by weight of 3-fluoro-4,6-dichlorotoluene and 24% by weight of 3-fluoro-2,6-dichlorotoluene were then separated off. The remaining residue was reused in a further batch.

After five repetitions of this example, the yield of 3-fluoro-4,6-dichlorotoluene and 3-fluoro-2,6-dichlorotoluene was 98% of theory.

EXAMPLE 3 (Comparative Example)

The same apparatus as described in Example 1 was charged with 110 g of 3-fluorotoluene. After addition of 220 mg of iron(III) chloride and 110 mg of sulphur, chlorine was introduced at 20° C. while stirring until only 1% by weight of the monochloro derivative was present. A mixture containing 59% by weight of 4,6-dichloro- 3-fluorotoluene and 31% by weight of 2,6-dichloro-3-fluorotoluene was obtained.

In the distillation, a first fraction of 20 g was taken off and fed to the next batch. 130 g of the isomer mixture were obtained as main fraction, the remaining residue was likewise reused.

After repeating the procedure five times, the yield was 86% of theory for the mixture.

EXAMPLE 4 (Comparative Example)

The same apparatus as described in Example 1 was charged with 110 g of 3-fluorotoluene. After addition of 750 mg of iron(III) chloride and 150 mg of 2,3-dihydro-5H-benzo[b][1,4]thiazepin-4-one, chlorine was introduced at 20° C. while stirring until only 1% by weight of the monochloro derivative was present. A mixture containing 43% by weight of 4,6-dichloro-3-fluorotoluene and 43% by weight of 2,6-dichloro-3-fluorotoluene was obtained.

The reaction mixture was worked up as described in Example 2.

In the distillation, a first fraction of 20 g was taken off and fed to the next batch. 120 g of the isomer mixture were obtained as main fraction, the remaining residue was likewise reused.

After repeating the procedure five times, the yield was 80% of theory for the mixture.

What is claimed is:

1. A process for preparing 3-fluoro-4,6-dichlorotoluene with reduced formation of 3-fluoro-2,6-dichlorotoluene, in which 3-fluorotoluene is chlorinated in the presence of Friedel-Crafts catalyst and sulphur to give a mixture containing 3-fluoro-6-chlorotoluene and 3-fluoro-4-chlorotoluene and this is chlorinated in the presence of Friedel-Crafts catalyst and a thiazepine compound to give 3-fluoro-4,6-dichlorotoluene.

2. The process of claim 1, in which the Friedel-Crafts catalyst used in both reaction stages is iron(III) chloride, antimony(III) chloride, antimony(V) chloride or aluminium chloride and in the first reaction stage is used in an amount of from 0.05 to 5% by weight (based on 3-fluorotoluene) and in the second reaction stage is used in an amount of from 0.1 to 10% by weight (based on 3-fluoro-chlorotoluenes).

3. The process of claim 1, in which from 0.05 to 5% by weight of sulphur (based on 3-fluorotoluene) is used.

4. The process of claim 1, in which the first reaction stage is carried out at from 0° to 60° C. and from 0.8 to 1.1 mol of chlorine is introduced per mol of 3-fluorotoluene.

5. The process of claims 1, in which low-boiling by-products, are separated off prior to the second reaction stage.

6. The process of claim 5, in which the low-boiling by-products are volatile sulphur compounds.

7. The process of claim 1, in which the thiazepine compound used is one of the formulae (I) to (VII)

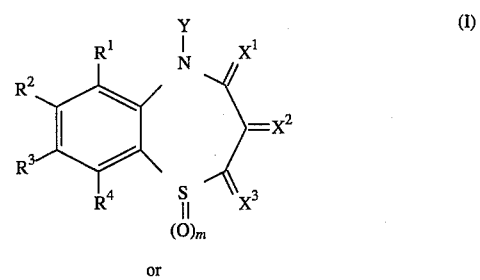

(I)

or

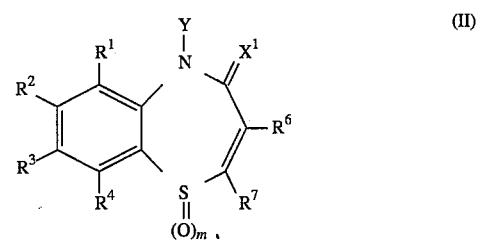

(II)

or

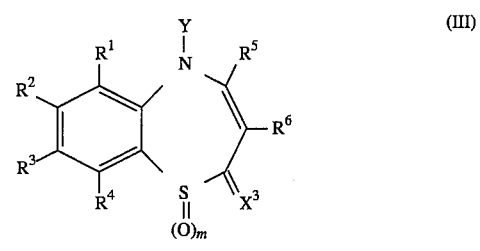

(III)

or

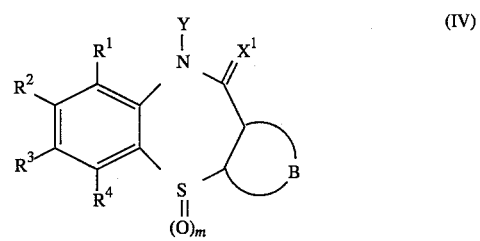

(IV)

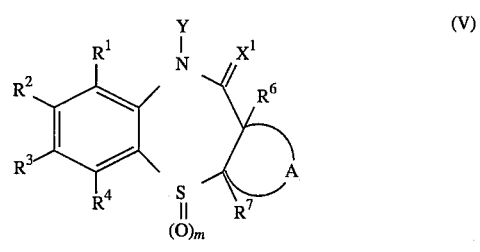

(V)

or

-continued

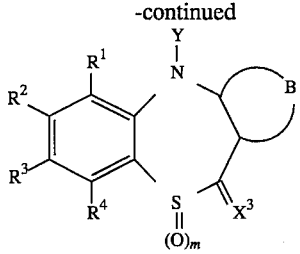
(VI)

or

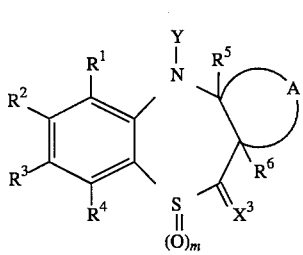
(VII)

in which

R¹, R², R³, R⁴ are identical or different and represent hydrogen, hydroxy, amino, cyano, halogen, nitro, nitroso, sulphonyl, sulphoxyl, tosyl, mercapto, carboxyl, carboxyamide, carbalkoxy, dithiocarboxyl, thiocarboxylamide, dithiocarbalkoxy, optionally substituted alkyl, aryl, heteroaryl, alkoxy, aryloxy, heteroaryloxy, acyloxy, alkylthio, arylthio, heteroarylthio, acylthio, acyl, thioacyl or acylamino or among one another form one or more saturated or unsaturated, optionally substituted isocyclic or heterocyclic carbon rings having up to 8 carbon atoms, Y is hydrogen, optionally substituted alkyl, aryl, heteroaryl, acyl, thioacyl, acyloxy, arylamino or acylamino, X¹, X² and X³ are, independently of one another, each one of the following groups:

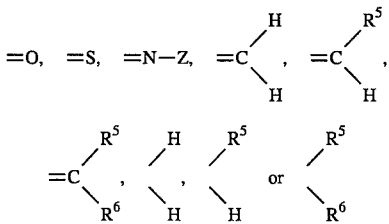

R⁵, R⁶ and R⁷ are identical or different and are as defined for R¹ to R⁴, with the exception that they do not form a cyclic ring among one another, Z is as defined for Y, with the exception that Z is not H, A represents the anellation of an optionally substituted, saturated, isocyclic or heterocyclic ring having up to 8 carbon atoms, B represents the anellation of an optionally substituted, unsaturated, isocyclic or heterocyclic ring having up to 8 carbon atoms, and m is 0 or 1, and is used in an amount of from 0.02 to 2% by weight (based on 3-fluoro-chlorotoluenes).

8. The process of claim 1, in which the second reaction stage is carried out at from 50° to 120° C. and from 0.8 to 1.0 mol of chlorine is introduced per mol of 3-fluorochlorotoluenes.

9. The process of claim 1, in which after completion of the second reaction stage the thiazepine compound is separated off and again added to a further batch.

10. The process of claim 1, in which the isomers 3-fluoro-4,6-dichlorotoluene and 3-fluoro-2,6-dichlorotoluene present in the reaction mixture after the second reaction stage are separated from each other by distillation.

11. The process of claim 1, in which the 3-fluorodichlorotoluene isomers present after completion of the second reaction stage are subjected to a side-chain chlorination and isomer separation is carried out from the benzal chloride/ benzotrichloride mixture.

\* \* \* \* \*